United States Patent [19]

della Valle et al.

[11] Patent Number: 5,183,807

[45] Date of Patent: Feb. 2, 1993

[54] USE OF MONOSIALOGANGLIOSIDE GM, TO PREVENT THE DEVELOPMENT OF TOLERANCE TO THE ANALGESIC EFFECT OF MORPHINE AND RELATED DRUGS

[75] Inventors: Francesco della Valle, Padua; Gino Toffano, Montegrotto Terme, both of Italy

[73] Assignee: FIDIA S.p.A., Abano Terme, Italy

[21] Appl. No.: 723,280

[22] Filed: Jun. 28, 1991

[30] Foreign Application Priority Data

Jun. 29, 1990 [IT] Italy .............................. 20822 A/90

[51] Int. Cl.$^5$ .................. A61K 31/70; A61K 31/715; A61K 31/44
[52] U.S. Cl. ...................................... 514/25; 514/54; 514/282
[58] Field of Search ............................ 514/25, 282, 54

[56] References Cited

U.S. PATENT DOCUMENTS

| | | | |
|---|---|---|---|
| 4,476,119 | 10/1984 | della Valle et al. | 514/25 |
| 4,940,694 | 7/1990 | della Valle et al. | 514/25 |
| 5,045,532 | 9/1991 | della Valle et al. | 514/25 |
| 5,066,496 | 11/1991 | Szabo et al. | 514/25 |

*Primary Examiner*—Frederick E. Waddell
*Assistant Examiner*—Raymond J. Henley, III
*Attorney, Agent, or Firm*—Birch, Stewart, Kolasch and Birch

[57] ABSTRACT

The use of monosialoganglioside $GM_1$, of its pharmacologically acceptable salts and of its internal ester derivative for the preparation of pharmaceutical compositions for preventing the development in man of tolerance to the analgesic effect of morphine, of chemically correlated opiates, and of methadone and its derivatives is described.

8 Claims, No Drawings

USE OF MONOSIALOGANGLIOSIDE GM, TO PREVENT THE DEVELOPMENT OF TOLERANCE TO THE ANALGESIC EFFECT OF MORPHINE AND RELATED DRUGS

FIELD OF THE INVENTION

The present invention relates to the use of the $GM_1$ monosialoganglioside, of its pharmacologically acceptable salts and of its internal ester derivative, for the preparation of pharmaceutical compositions for preventing the development in man of tolerance to the analgesic effect of morphine, of the chemically correlated opiates, and of methadone and its derivatives.

PRIOR ART

As is known, the continuous use of opiates, and in particular of morphine, leads to the development of tolerance thereto in man. The daily repeated administration of morphine leads, in variable measure, to the development of tolerance to the therapeutic effects of the drug, the degree of which will depend on the frequency and size of the administered dose.

The tolerance takes place when, after repeated administrations, the same drug dose produces lower effects, or when progressively larger doses must be administered in order to reach the effects obtained with the starting dose.

Even if the tolerance does not by itself modify the possibility of pursuing the use of the drug, it necessarily modifies the way of using it, as the amount to be taken to obtain a certain effect must be increased. The use of increasing amounts of morphine and of correlated opiates may lead to the impossibility of therapeutically utilizing said substances because of the increased toxic and collateral effect which takes place following the administration of high doses.

Gangliosides, pertaining to the class of glycosphingolipids (glycolipids) being, more precisely, glycosphingolipids containing sialic acid, and having, chemically, a structure consisting of a saccharide moiety to which a ceramide and a sialic group are bound, are known.

The saccharide moiety consists of at least a galactose or glucose and at least an N-acetyl-glucosamine or N-acetylgalactosamine, and these components are bound together by glucoside bonds.

Numerous gangliosides have been identified, which are particularly abundant in nerve tissues, particularly in cerebral tissue.

Among the numerous gangliosides which were isolated from ganglioside mixtures extracted from cerebral bovine tissues, the $GM_1$ ganglioside is present, which shows the following structure:

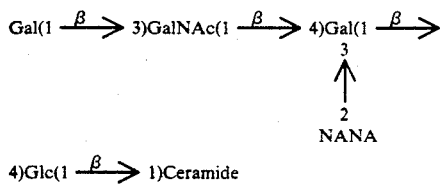

where Glc is an abbreviation for glucose, GalNAc for N-acetylgalactosamine, Gal for galactose, and NANA for N-acetylneuraminic acid.

Other possible denominations for the $GM_1$ ganglioside are:
monosialotetraexosylganglioside, sodium salt;
$II^3$-α-N-acetyl neuraminosyl gangliotetraglycosyl ceramide, sodium salt (IUPAC-IUB denomination);
$II^3$-α-NeuAc-GgOse$_4$Cer, sodium salt (IUPAC-IUB abbreviation);
Chemical Abstracts register: RN 37758-47-7

The $GM_1$ symbol is in conformity with the Svennerholm system (Svennerholm L.: J. Neurochem., 19, 613–623, 1963).

As the gangliosides are mainly associated with neuronal membranes (Ando S.: Gangliosides in the nervous system, Neurochem. Int. 5, 507–537, 1983), the hypothesis was made that they may play a role in the transfer of information through said membranes (Fishman P. H., Brady R. O.: Science, 194, 906–915, 1976). In particular, the monosialoganglioside $GM_1$ is implied in the neuronal differentiation processes in the mouse cerebellum (Willinger M., Schachmer M.: Dev.Biol. 74, 101–107, 1980) and in the induction of meganeurites in cortical rat neurons (Purpura D. P., Baker H. J.: Brain Res., 143, 13–26, 1977).

A specific $GM_1$ ganglioside role in facilitating the formation of synaptic contacts was suggested following experiments which evidenced how the enrichment in $GM_1$ facilitates the formation of neuromuscular junctions in nerve-muscle co-cultures (Obata K., Handa S.: "Integrative Control Functions of the Brain" Ed. Ito et al, 2, 5–14 (1979)).

$GM_1$ is a biological substance which is extracted from the bovine brain, and its sodium salt may be isolated as a highly purified product following the procedures described by Tettamanti et al.: Biochimica & Biophysica Acta, 296, 160–170, 1973, or as described in the Italian patent 1.046.051 granted Jun. 30, 1980.

The internal ester $GM_1$ ganglioside derivative may be prepared as described in the U.S. Pat. No. 4,476,119 and the European Patent EP 0072722.

Ample documentation exists on the ability on the part of gangliosides to favorably influence the functional recovery of damaged peripheral nervous system (PNS) and central nervous system (CNS), by involvement of specific membrane mechanisms and interaction with neurotrophic factors, as evidenced by in vitro studies on neuronal cultures (Doherty P. et al.: "Ganglioside $GM_1$ does not initiate but enhances neurite regeneration of nerve growth factor—dependent sensory neurons", J. Neurochem. 44, 1259–1265, 1985).

In particular, the effects were reported of the ganglioside mixture on the PNS in traumatic neuropathies (Gorio A. et al.: "Motor nerve sprouting induced by ganglioside treatment. Possible implications for gangliosides on neuronal growth", Brain Res: 7, 236, 1980), metabolic neuropathies (Norido F. et al.: "The Development of diabetic neuropathy in the C57B1/Ks (db/db) mouse and its treatment with gangliosides", Exp. Neurol., 83, 221, 1984) and toxic neuropathies (Di Gregorio F. et al.: "Efficacy of ganglioside treatment in reducing functional alterations induced by vincristine in rabbit peripheral nerves", Cancer Chemother. Pharmacol., 26, 31–36, 1990). As to the CNS, the positive recovery effects induced by the monosialoganglioside $GM_1$ and by its internal ester in models of ischemy (Karpiak S.E. et al.: "Ganglioside reduction of CNS ischemy injury". CRC Critical Rev. in Neurobiology, Vol. 5 Issue 3, 1990), of traumatic lesions (Toffano G. et al.: "Chronic $GM_1$ ganglioside treatment reduces dopamine cell body degeneration in the substantia nigra after unilateral hemitransection in rat", Brain Res., 296, 233-239, 1984) and neuronotoxic lesions (Johnsson J. et. al.: "Effect of $GM_1$ ganglioside on neonatally neurotoxin induced degeneration of serotin neurons in the rat brain", Develop. Brain Res., 16, 171-180, 1984b) at the level of different neuronal systems in various animal species have been amply described.

No analgesic effect of $GM_1$, or of its internal ester derivative at the CNS level, nor any interference on the part of $GM_1$ or of its internal ester derivative with the activity of the opiates in general, of morphine in particular, and of methadone and its derivatives, was ever described, which could suggest their use according to the present invention.

We now have surprisingly found that $GM_1$, its pharmaceutically acceptable salts and its internal ester derivative are active in inhibiting the development in man of a tolerance to the analgesic effect of morphine, of the chemically correlated opiates, of methadone and of its derivatives.

This is surprising, in view of the fact that $GM_1$, and the other gangliosides, do not have by themselves any analgesic effect at the CNS level, and that it was therefore impossible to foresee any interference with the morphine-similar analgesics. Opiates chemically correlated with morphine are e.g. heroine, etorphine, thebaine, codeine, pentazocine, etc., while a methadone derivative is for instance methadyl acetate.

In order to demonstrate the activity of $GM_1$ in the use according to the present invention, we have performed a series of tests employing the $GM_1$ sodium salt, having MW 1568.9, isolated from bovine brain according to the method described in the Italian patent n. 1.046.051 granted Jun. 30, 1980.

In particular, two tests were performed on the mouse, in relation to the evaluation of:
analgesic effect, through the hot plate test;
mortality, expressed as LD 50.

$GM_1$ was solubilized, in 100 mg per 1 ml solution doses, in physiological saline solution in the presence of phosphate buffer having the following composition:

| | |
|---|---|
| $Na_2HPO_4.12\ H_2O$ | 3 g |
| $NaH_2PO_4.2\ H_2O$ | 0.25 g |
| NaCl | 8 g |
| Distilled water to | 1000 ml |

The test was performed on male Swiss mice of a weight between 23 and 28 g divided in 4 groups.

Test on the Development of Tolerance to the Analgesic Effect of Morphine

The animals of groups 1 and 2 did not receive any treatment in the first period, while in the second period they were treated for 13 days respectively with saline solution and with $GM_1$. The animals of group 3 were treated in the first period of 13 days with saline solution and in the second period of 6 days with saline solution in association with morphine.

The animals of Group 4 were treated for a 13 days first period with $GM_1$ at the dose of 30 mg/kg/d i.p.; the treatment was then continued for an additional 6 days, associated, however, with a morphine administration twice a day with doses increasing from 10 mg/kg/d to 200 mg/kg/d s.c.

The analgesic effect, and the subsequent development of morphine tolerance were evaluated by a hot plate test. This test, based on the pain reaction of the animal to a thermal stimulus (Berkowitz B. A. et al.: "Nitrous oxide analgesia: reversal by naloxone and development of tolerance", J. Pharmacol. exp. Ther., 203, 539-547, 1977), is specific for evaluating the central analgesic activity of a drug.

Two days prior to the tests, the animals were selected among the ones which, put individually on a hot plate (Technilab Hot-plate—U. Basile, Milan) kept at a constant temperature of 52.5° C., showed a constant reaction time of between 5 and 10 seconds (basal pain sensitivity threshold).

As indication of a reaction to the stimulus, a jump or the lifting and licking of the front paws was interpreted.

The analgesic activity was evaluated at the 20th day from the start of the treatment, on the basis of the increase in the reaction time of each animal after 15, 30 and 45 minutes from the treatment with a dose of morphine (10 mg/kg s.c.) with respect to basal values determined 30 minutes prior to the treatment (0 time).

The values obtained were then expressed as percent increase of the pain threshold after morphine administration.

RESULTS

As evident from the data of Table 1:
The animals in the control group (Group 1) after the morphine treatment developed a rise in the pain threshold;
the treatment with $GM_1$ (Group 2) did not modify the rise in the pain threshold; therefore, $GM_1$ by itself does not have analgesic effect;
the animals of group 3 were found completely tolerant to the morphine analgesy after 6 days of treatment;
the mice pre-treated with $GM_1$ (Group 4) developed a significantly lower tolerance.

TABLE 1

Effect of the chronic treatment with $GM_1$ in the morphine tolerance

| | | Chronic Treatment | | | % Increase of the pain threshold after morphine administration (10 mg/kg s.c.) | |
|---|---|---|---|---|---|---|
| | | 1st period | | 2nd period | | |
| Gr. | N | DD | Drug | DD | Drug | 15' | 30' | 45' |
| 1 | 93 | — | — | 13 | Saline | 67 ± 6 | 67 ± 7 | 44 ± 6 |
| | | | | | | | $p < 0.05$ | $p < 0.05$ |
| 2 | 92 | — | — | 13 | $GM_1$ | 68 ± 6 | 98 ± 7 | 69 ± 7 |
| 3 | 89 | 13 | Saline | 6 | Sal + Morph. | 1 ± 4 | 6 ± 4 | 5 ± 3 |
| | | | | | | | $p < 0.05$ | $p < 0.05$ |
| 4 | 80 | 13 | $GM_1$ | 6 | $GM_1$ + Morph. | 43 ± 5 | 39 ± 6 | 37 ± 5 |

Gr = Group; N = number of animals; DD = Days; Saline = saline solution 10 mg/kg i.p. or s.c.

The morphine administration was in fact capable of inducing in these mice a significant analgesic effect, while in the controls it was completely inefficient.

MORTALITY EVALUATION

After the analgesic effect evaluation we determined the morphine LD 50, first for a group of mice made tolerant to morphine by the administration of saline solution and morphine, and then for another group of mice pre-treated for 20 days with $GM_1$ and successively treated with $GM_1$ in association with a morphine dose equal to the one administered to the other group. As is known, the LD 50 in mice tolerant to morphine is higher than for non tolerant mice (Goodman and Gilman: "The pharmacological basis of therapeutics": Eds. Goodman Gilman et al. page 543). Table 2 reports the data.

TABLE 2

Effects of the chronic $GM_1$ treatment on the lethality induced by morphine

| Treatment | N | Morphine DL 50 (mg/kg) i.p. |
|---|---|---|
| — | 15 | 342 (246–479) |
| Saline (10 ml/kg) i.p. | 37 | 320 (277–370) |
| $GM_1$ (30 mg/kg) i.p. | 35 | 367 (320–442) |
| Saline + Morphine | 38 | 686 (543–867) |
| $GM_1$ + Morphine | 37 | 487 (292–810) |

N = number of animals

The figures in parenthesis show the LD values minimal and maximal found for that group of animals.

From the data reported in Table 2 it is evident that:
LD 50 increases significantly from 320 to 686 mg/kg in tolerant mice;
LD 50 in mice pretreated with $GM_1$ for 20 days increases from 367 to 487, the difference is therefore not significant.

These results, obtained by evaluating the effect on pain threshold and on lethality, show that the $GM_1$ pre-treatment is inhibits the development of tolerance to the morphine effect. The use of $GM_1$, of its pharmaceutically acceptable salts and of its internal ester derivative, for the preparation of pharmaceutical compositions suitable to prevent the development in man of tolerance to the analgesic effect of morphine, of the chemically correlated opiates, and of methadone and its derivatives, may be of considerable usefulness at the clinical level.

In fact, the use of morphine for curing intolerable pains, in particular in terminal cancer cases, is limited by the development of tolerance, thus making it necessary to use continuously increasing doses with the ensuing increase in collateral effects and in the toxicity due to morphine. A further possible application of the compositions according to the invention is in the cure of drug addition.

The pharmaceutical compositions according to the present invention may have an active principle content of between 10 and 400 mg, in association with one or more pharmacologically acceptable eccipients, and may be administered to man per os or parenterally, preferably intramuscularly, intravenously or subcutaneously.

The pharmaceutical compositions according to the present invention may preferably be administered for a period of at least 8 days to starting the treatment with opiates in general, morphine in particular, and methadone or its derivatives, or they may be administered contemporaneously with or successively to the treatment, for a period of at least 8 days. The administered dose of active principle will depend on the effects desired and on the selected way of administration and will be of between 0.15 and 6 mg/kg/day, equivalent to approximately between 10 and 400 mg/day, preferably of 0.6 mg/kg/day corresponding to approximately 40 mg/day.

For purely descriptive and not limitative purposes, we report a few examples of pharmaceutical compositions according to the present invention.

EXAMPLE 1

A vial comprises:

| | |
|---|---|
| monosialotetraexosylganglioside $GM_1$ sodium salt | 20.0 mg |
| bibasic sodium phosphate 12 $H_2O$ | 6.0 mg |
| monobasic sodium phosphate 2 $H_2O$ | 0.5 mg |
| sodium chloride | 16.0 mg |
| water for injectable preparations to | 2.0 ml |

EXAMPLE 2

A vial comprises:

| | |
|---|---|
| monosialotetraexosylganglioside $GM_1$ sodium salt | 40.0 mg |
| bibasic sodium phosphate 12 $H_2O$ | 6.0 mg |
| monobasic sodium phosphate 2 $H_2O$ | 0.5 mg |
| sodium chloride | 16.0 mg |
| water for injectable preparations to | 2.0 ml |

EXAMPLE 3

A vial comprises:

| | |
|---|---|
| monosialotetraexosylganglioside $GM_1$ sodium salt | 100 mg |
| bibasic sodium phosphate 12 $H_2O$ | 15.0 mg |
| monobasic sodium phosphate 2 $H_2O$ | 1.25 mg |
| sodium chloride | 40.0 mg |
| water for injectable preparation to | 5.0 ml |

We claim:

1. A method for preventing the development of tolerance to the analgesic effect of morphine, of chemically correlated opiates and of methadone and its derivatives, which comprises administering to patients in need thereof, either prior to, contemporaneously with or successively to the analgesic administration of said compounds, a therapeutically effective amount of the ganglioside $GM_1$, its pharmacologically acceptable salts or its internal ester derivative, alone or together in mutual association.

2. The method according to claim 1, wherein the amount of $GM_1$ administered is from 0.15 to 6 mg/kg/day.

3. The method according to claim 2, wherein the amount of $GM_1$ administered corresponds to 0.6 mg/kg/day.

4. The method according to claim 1, wherein $GM_1$ is administered for a period of at least 8 days prior to the analgesic administration of morphine, of chemically correlated opiates, or of methadone and its derivatives.

5. The method according to claim 1, wherein $GM_1$ is administered at least 8 days contemporaneously with or successively to the analgesic administration of morphine, of chemically correlated opiates, or of methadone and its derivatives.

6. The method according to claim 1, wherein $GM_1$ is administered orally or parenterally.

7. The method according to claim 1, wherein said patients are terminal cancer patients.

8. The method according to claim 1, wherein said patient are drug addicts.

* * * * *